(12) United States Patent
Bitar

(10) Patent No.: US 9,993,505 B2
(45) Date of Patent: *Jun. 12, 2018

(54) INNERVATION OF ENGINEERED STRUCTURES

(71) Applicant: WAKE FOREST UNIVERSITY HEALTH SCIENCES, Winston-Salem, NC (US)

(72) Inventor: Khalil Bitar, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 843 days.

This patent is subject to a terminal disclaimer.

(21) Appl. No.: 14/375,812

(22) PCT Filed: Jan. 31, 2013

(86) PCT No.: PCT/US2013/024080
§ 371 (c)(1),
(2) Date: Jul. 31, 2014

(87) PCT Pub. No.: WO2013/116479
PCT Pub. Date: Aug. 8, 2013

(65) Prior Publication Data
US 2014/0377232 A1    Dec. 25, 2014

Related U.S. Application Data

(60) Provisional application No. 61/592,871, filed on Jan. 31, 2012, provisional application No. 61/592,890, filed on Jan. 31, 2012.

(51) Int. Cl.
| | |
|---|---|
| *C12N 5/00* | (2006.01) |
| *C12N 5/02* | (2006.01) |
| *A61K 35/34* | (2015.01) |
| *A61L 27/20* | (2006.01) |
| *C12N 5/077* | (2010.01) |
| *A61L 27/38* | (2006.01) |
| *A61L 27/50* | (2006.01) |
| *C12N 5/0797* | (2010.01) |
| *A61F 2/04* | (2013.01) |
| *A61F 2/08* | (2006.01) |

(52) U.S. Cl.
CPC ............. *A61K 35/34* (2013.01); *A61F 2/04* (2013.01); *A61F 2/08* (2013.01); *A61L 27/20* (2013.01); *A61L 27/3826* (2013.01); *A61L 27/3873* (2013.01); *A61L 27/50* (2013.01); *C12N 5/0068* (2013.01); *C12N 5/0623* (2013.01); *C12N 5/0661* (2013.01); *A61F 2002/045* (2013.01); *A61L 2430/30* (2013.01); *C12N 2501/999* (2013.01); *C12N 2533/54* (2013.01); *C12N 2533/72* (2013.01)

(58) Field of Classification Search
None
See application file for complete search history.

(56) References Cited

U.S. PATENT DOCUMENTS

| | | |
|---|---|---|
| 7,029,689 B2 | 4/2006 | Berglund et al. |
| 7,368,279 B2 | 5/2008 | Bitar et al. |
| 2003/0031651 A1 | 2/2003 | Lee et al. |
| 2003/0072741 A1 | 4/2003 | Berglund et al. |
| 2004/0197375 A1 | 10/2004 | Rezania et al. |
| 2005/0209687 A1 | 9/2005 | Sitzmann et al. |

(Continued)

FOREIGN PATENT DOCUMENTS

| | | |
|---|---|---|
| JP | 2004528101 A | 9/2004 |
| WO | 2002087411 A2 | 11/2002 |

(Continued)

OTHER PUBLICATIONS

Sundararajan et al., Porus chitosan scaffolds for tissue engineering. Biomaterials. Jun. 1999;20(12): 1133-1142.
PCT International Preliminary Report on Patentability and Written Opinion, PCT/US2013/024080, dated Aug. 14, 2014 (10 pages).
Raghavan, S. et al. Successful Implantation of Bioengineered, Intrinsically Innervated, Human Internal Anal Sphincter:, Gastroenterology, Jul. 2011, vol. 141, pp. 310-319. See materials and methods, pp. 311-315; results, p. 312; figure 1.
PCT International Search Report and Written Opinion, PCT/US2013/024080, dated Jun. 2, 2013 (13 pages).

(Continued)

*Primary Examiner* — Chris R Tate
*Assistant Examiner* — Douglas F White
(74) *Attorney, Agent, or Firm* — Thomas J. Engellenner; Reza Mollaaghababa; Pepper Hamilton LLP

(57) ABSTRACT

Methods of generating an innervated muscle structures are disclosed as well as bioengineered structures for tissue repair or regeneration. The methods can include the steps of obtaining populations of smooth muscle cells and neuronal progenitor cells and then seeding the cells together onto a matrix material, followed by culturing the seeded cells to form an innervated smooth muscle cell construct of directionally oriented smooth muscle cells. In one embodiment, the neuronal progenitor cells can be seeded first as neurospheres in a biocompatible solution, e.g., a collagen/laminin solution, and allowed to gel. Next, a second suspension of smooth muscle cells can be deposited as separate layer. Multiple layer structures of alternating muscle or neuron composition can also be formed in this manner. Differentiation of the neuronal progenitor cells can be induced by exposure to a differentiation medium, such as Neurobasal A medium and/or exposure to a differentiating agent, such as B-27 supplement. The innervated muscle structures can be disposed around a tubular scaffold, e.g., a chitosan-containing tube and further cultured to form tubular, bioengineered structures and two or more innervated muscle structures can be joined together to form an elongate composite structure.

15 Claims, 9 Drawing Sheets

(56) References Cited

U.S. PATENT DOCUMENTS

| | | | |
|---|---|---|---|
| 2006/0153815 A1* | 7/2006 | Seyda | A61L 27/3604 424/93.7 |
| 2007/0025972 A1* | 2/2007 | Rodriguez | C12N 5/0667 424/93.7 |
| 2008/0031850 A1* | 2/2008 | Bader | A61K 35/407 424/85.2 |
| 2010/0131075 A1 | 5/2010 | Ludlow et al. | |
| 2010/0184183 A1* | 7/2010 | Schussler | A61L 27/24 435/177 |

FOREIGN PATENT DOCUMENTS

| | | |
|---|---|---|
| WO | 2010/040129 A2 | 4/2010 |
| WO | 2010072417 A2 | 7/2010 |
| WO | 2011/102991 A1 | 8/2011 |
| WO | 2011102991 A1 | 8/2011 |
| WO | 2011119804 A2 | 9/2011 |

OTHER PUBLICATIONS

Supplementary European Search Report for corresponding European Application 13743292.8 dated Aug. 18, 2015.

Madihally, Sundararajian et al. "Porous Chitosan Scaffolds for Tissue Engineering", Biomaterials 20 pp. 1133-1142 (1999).

Raghavan, Shreya et al. Successful Implantation of Bioengineered, Intrinsically Innervated, Human Internal Anal Sphincter.

Zhang, Ling et al. "A Sandwich Tubular Scaffold Derived From Chitosan for Blood Vessel Tissue Engineering" Wiley Periodicals, Inc. pp. 278-284.

L'Heurex, Nicolas et al., "A completely Biological Tissue-Engineered Human Blood Vessel", The FASEB Journal, vol. 12, pp. 47-56 (Jan. 1998).

Buijtenhuijs et al., "Tissue engineering of blood vessels: characterization of smooth-muscle cells for culturing on collagen-and-elastin-based scaffolds." Biotechnol Appl Biochem. Apr. 2004;39(Pt 2):141-9.

International Search Report and Written Opinion received in PCT/US2013/024024 dated May 15, 2013; 12 pages.

International Preliminary Report on Patentability received in PCT/US2013/024024 dated Aug. 5, 2014; 8 pages.

Office Action received in EP Application No. 13743292.8 dated Jul. 18, 2017; 6 pages.

Office Action received in JP Application No. 2014-555699 dated Jul. 25, 2017; 5 pages.

Somara et al., Bioengineered Internal Anal Sphincter Derived From Isolated Human Internal Anal Sphincter Smooth Muscle Cells. Gastroenterology. Jul. 2009; 137(1): 53-61.

* cited by examiner

INNERVATION OF ENGINEERED STRUCTURES

REFERENCE TO RELATED APPLICATIONS

This application is based upon and claims the priority of U.S. Provisional Patent Application No. 61/592,890, entitled "Innervation of Engineered Structures, and U.S. Provisional Patent Application No. 61/592,871 filed Jan. 31, 2012, entitled "Tubular Bioengineered Smooth Muscle Structures," which are both hereby incorporated in its entirety by reference.

GOVERNMENT SUPPORT

This invention was made with government support under grants NIH RO1DK071614 and NIH RO1DK042876 awarded by The National Institute of Health. The United States Government has certain rights in the invention.

FIELD OF THE INVENTION

The present invention concerns tissue engineering and in particular, innervation of tissue engineered structures.

BACKGROUND OF THE INVENTION

Innervation is extremely important for maintaining the functionality of almost every part of the human body. Innervation of the gastrointestinal (GI) tract is extremely important for smooth muscle cells to maintain their phenotype and to perform their motor function, i.e., generating the forces necessary for fluid movement through the GI tract.

Upon nerve injury, muscle atrophy is commonly observed. Patients who suffer from different degrees of paralysis of the gut whether due to aging or diabetes (gastroparesis) also lack the neural elements as well as exhibit muscle atrophy. Similarly, children born with aganglionic gut disorders (e.g., Hirschsprung's disease) exhibit nerve degeneration.

Tissue engineering has been proposed to restore the function of diseased or damaged GI tract components by replaced degenerative muscle with new muscle structures. However, regenerating muscle using extracellular matrices seeded with muscle or muscle progenitor cells can replace a maximum about 10 percent of the lost muscle mass. Even with strenuous rehabilitation there is typically only about 30 percent recuperation of force generation.

For example, a functional gastric mucosa has been reported using gastric epithelial organoid units seeded on composite PLGA meshes to replace the native stomach of rats. The regeneration of stratified smooth muscle layers with the proper orientation, however, remains a challenge. Moreover, restoration of functional motility was not demonstrated in prior studies, highlighting the biggest challenge yet in functional tissue engineering of the GI neuromusculature.

Reconstruction of the stomach by tissue engineering is also a challenge. Aspects of bladder tissue engineering, whereby de-novo bladder reservoirs are manufactured with a variety of biomaterials, have been proposed as templates to re-engineer the musculature of the stomach. In stomach reconstruction, implantable gastric stimulation units, already commonly used in bariatric surgeries and in gastroparesis to stimulate enteric neurons or simulate gastric electrical rhythm, have been proposed as building blocks for stomach reconstruction. A report by Micci et al. demonstrates that the transplantation of CNS-derived neuronal progenitor cells can repopulate nitrergic neurons as well as improve gastric function in the pylorus of a rodent model of gastroparesis.

Tissue engineering also offered a possible advance to the bowel lengthening surgeries commonly carried out in short bowel syndrome. Collagen sponge scaffolds seeded with autologous smooth muscle cells have been successfully implanted as patch grafts in canine models. These patch grafts regenerated the mucosal and intestinal epithelial layers along with the villi structures. The major problem encountered with these grafts, however, was shrinkage. Dunn et al. used pseudo-tubular structures formed from collagen sponge scaffolds seeded with intestinal smooth muscle cells. The tubular structures were neovascularized within a month after prevascularization in the omentum. Unfortunately, these techniques did not regenerate the enteric neuronal layers, and the smooth muscle cells demonstrated a phenotypic switch to their non-contractile forms.

Tissue engineered small intestinal constructs, likewise, have not achieved the alignment of the smooth muscle cells or their innervation that appears to be crucial to generating appropriate force and motility to facilitate nutrient absorption.

Regeneration of colon segments is similarly elusive. The colon is contiguous with the small intestine, facilitating water absorption and excretion of stool. Loss of colonic segments by surgical resections e.g., to treat aganglionosis (Hirschsprung's Disease) or inflammation significantly alters colonic motility. Disruption of colonic motility alters transit time, resulting in constipation or diarrhea. The idiopathic nature of some of these disease states poses a strong demand for in vitro tissue engineered models of colon, where investigations can be carried out on individual components (smooth muscle, enteric neurons, interstitial cells and mucosa) to understand alterations in pathophysiological conditions. Moreover, alterations in peristalsis and segmental contractions of the colon have direct implications on an individual's quality of life.

Recently, Vacanti et al. reported a tissue engineered colon construct using composite poly lactic and glycolic acid polymers seeded with organoid units isolated from the sigmoid colon. They demonstrated that the tissue engineered conduits have significant absorptive capacity when implanted into animals, but there was no direct measurement of peristalsis or motility.

Phasic neuromuscular structures of the GI tract contain orthogonal layers of smooth muscle, interlaced with enteric neuronal plexuses. They are also associated with the interstitial cells of Cajal (ICC) and the specialized mucosal layers. Propagating peristaltic waves define the phasic nature of this neuromusculature. Peristaltic waves encompass contraction and relaxation of both the circular and longitudinal smooth muscle layers. The neuronal components as well as the ICC generate electrical activity for the coordination of peristalsis. This activity is coupled with intracellular biochemical events in the smooth muscle layers to regulate gut motility. These mechanisms are additionally segmentally modulated by the release of different neurotransmitters from the enteric neuronal plexuses as well as the electrical activity from the ICCs.

In a recent study by Pan et al., neural crest progenitor cells isolated from neonatal rats were transplanted into the distal colon of a rat model of Hirschsprung's Disease. These cells differentiated into neurons and glia in the host colon. They also demonstrated rescue of neuronal mediated motility in the aganglionic host colon. Metzger et al. demonstrated that adult human gut derived enteric progenitor cells can repopulate segments of human aganglionic colon grown in organotypic cultures.

Although significant advances have been made in tissue engineering of phasic neuromuscular structures, many gaps exist in proposed techniques for regeneration of functional smooth muscle and enteric neuronal plexuses. Accordingly, there exists a need for better techniques for innervated engineered tissues.

SUMMARY OF THE INVENTION

Methods of generating innervated muscle structures are disclosed as well as bioengineered structures for tissue repair or regeneration. The methods can include the steps of obtaining a population of smooth muscle cells and neuronal progenitor cells and seeding the cells together onto a matrix material, followed by culturing the seeded cells to form an innervated smooth muscle cell construct of directionally oriented smooth muscle cells. In one embodiment, the neuronal progenitor cells can be seeded first as neurospheres in a biocompatible solution, e.g., a fibrin, collagen, or collagen/laminin solution, and allowed to gel. Next, a second suspension of smooth muscle cells can be deposited as a separate layer from the neuronal progenitor cell layer. Alternatively, the muscle cells can be seeded first and followed by a seeding of neuronal progenitor cells. Multiple layer structures of alternating muscle or neuron composition can also be formed in this manner. The smooth muscle and neuronal progenitor cell suspensions, either separately or together, can be deposited around a central post to induce formation of a tubular innervated smooth muscle cell construct. The innervated smooth muscle cell construct can then be disposed around a tubular scaffold, e.g., a chitosan-containing tube.

Neuronal progenitor cells have been identified to reside within both the central nervous system as well the enteric nervous system in embryonic as well as post-natal rodents and humans. Neural crest-derived stem cells have been shown to persist through adult development and are a potential source of autologous neuronal cells for re-engineering the gut neuromusculature. Advances in cell culture techniques demonstrated the isolation of enteric neuronal and glial progenitor cells expressing Ret and p75 markers that demonstrated the ability to differentiate into a number of mature enteric neuronal subtypes. A recent report by Kulkarni et al. focuses on nudging CNS-derived neuronal progenitor cells into an enteric phenotype by culturing them in the presence of gut derived soluble factors. Metzger et al. also demonstrated the reliable and reproducible isolation of enteric neuronal progenitor cells from adult human gut up to 84 years of age.

The neuronal progenitor cells can also be induced to differentiate. The neuronal progenitor cells can be cultured in a differentiation medium, such as Neurobasal A medium and/or exposed to a differentiating agent, such as B-27 supplement.

The methods of the present invention also include connecting two or more innervated muscle structures to form tubular, bioengineered structures by joining the innervated muscle structures together to form an elongated composite structure that can be stimulated to produce a travelling wave of contractions through the individual innervated tubular muscle structures.

In another aspect of the invention, it has been discovered that bioengineered three-dimensional fibrin-based models of colon allow self-alignment of circular smooth muscle layers concentrically around a patent lumen. These bioengineered tissues mimic native smooth muscle alignment and maintain aspects of colonic physiology like peristalsis, contraction and relaxation.

DETAILED DESCRIPTION OF THE INVENTION

Figure 1:
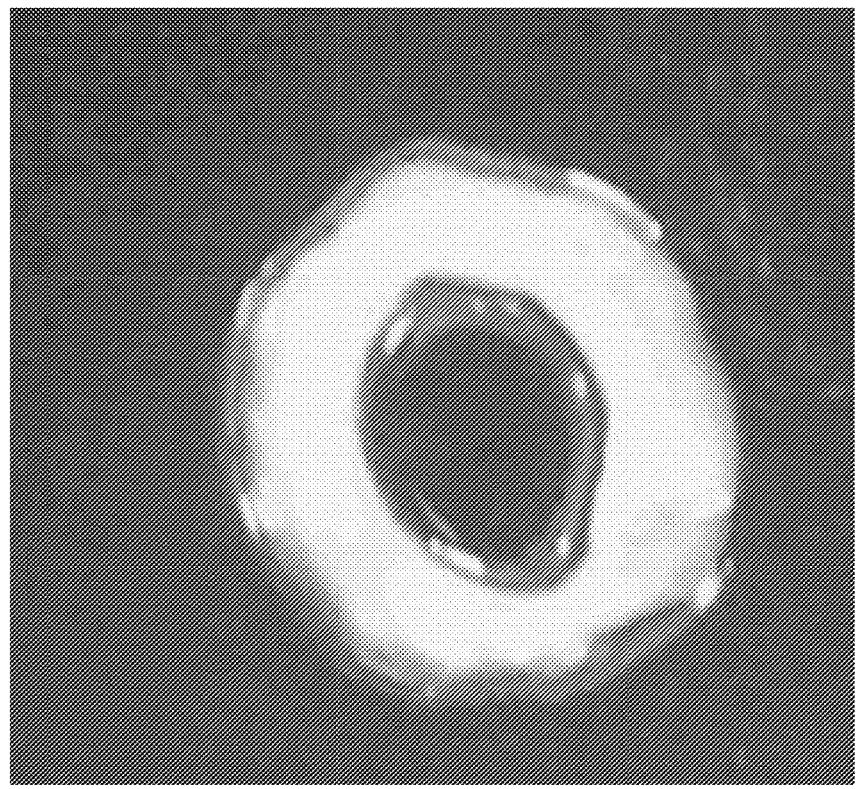
FIG. 1 shows a fully formed bioengineered innervated colon smooth muscle construct.

While designing replacements to GI tract components, it is important to keep in mind that motility patterns of the GI tract, though segmental, are inherently linked to one another and work in a highly coordinated fashion. An example of this phenomenon is the entry of the food into the esophagus leading to the relaxation of the lower esophageal sphincter (LES) to allow passage of food into the stomach. Tissue engineered LES constructs must possess the ability to generate myogenic basal tone. They must also be highly biocompatible and integrated with the existing neuronal network to transiently relax to allow food to pass from the esophagus to stomach, upon esophageal peristalsis.

Certain exemplary embodiments will be described to provide an overall understanding of the principles of the structure, function, manufacture, and use of the devices and methods disclosed herein. Those skilled in the art will understand that the devices and methods specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "subject" as used herein refers to any living organism, including, but not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

The terms "treating," "treatment" or "intervention" refer to the administration of one or more therapeutic agents or procedures to a subject who has a condition or disorder or a predisposition toward a condition or disorder, with the purpose to prevent, alleviate, relieve, alter, remedy, ameliorate, improve, affect, slow or stop the progression, slow or stop the worsening of the disease, at least one symptom of a condition or disorder, or the predisposition toward the condition or disorder.

Smooth Muscle Cells

One aspect encompasses generating bioengineered tubular tissues with smooth muscle rings. Physiological models of tubular structures made from smooth muscle tissues that are functionally similar to naturally occurring smooth muscle tissue. Organs or tissues that contain circular smooth muscle may be modeled using the culture system disclosed. Such organs and tissues include the components of the GI tract, e.g., the esophagus, stomach, duodenum, jejunum, ileum and colon. The methods and compositions of the present invention can also be useful in reconstruction of other luminal structures, such as the trachea, bronchial tubes, uterus, blood vessels, lymphatic vessels, urethra, glandular ducts, and the ciliary muscles of the eye.

The term "functionally similar" refers to a bioengineered tubular tissue or tubular tissue encompassing bioengineered smooth muscle rings having similar contractile force or a similar change in contractile isometric force as natural tubular tissue. Contractile force is measured as a peristaltic force or wave-like constrictions/relaxations of the smooth muscle cells of the tubular structure. An agonist may be useful for inducing a contractile response in a smooth muscle cell or induces electrical stimulation in a smooth muscle cell. Contractile response is defined as the decrease in the average length of a smooth muscle cell or smooth muscle tissue. Agonists of contraction include acetycholine, bombesin, substance P, protein kinase C (PKC), endothelins, other neurotransmitter and peptides.

Smooth muscle surrounds the supports of many of the hollow organs. For example, in the gut, smooth muscle surrounds the stomach and intestinal track. Contraction of this muscle mixes food and propels it along the digestive track. In the cardiovascular system, smooth muscle cells surround the walls of the arteries and large veins and functions to control the caliber of the vessels. Smooth muscle lacks the nearly uniform cell shape and lattice-like distribution of skeletal and cardiac muscle cells. However, smooth muscle cells do exhibit an elongated, bipolar cell shape. As a population, smooth muscle cells are organized along a similar axis in a series of overlapping cellular layers. This pattern of organization allows smooth muscle to exert contractile forces in a complex pattern.

The present invention can be employed using isolated primary smooth muscle cells or cell lines derived from such primary cells, tumors and the like. The cells used may be available smooth muscle cell lines such as internal intestinal or anal sphincter smooth muscle cell lines, airway smooth muscle cell lines and other commercially available smooth muscle cell lines. For example, cell lines derived from muscle may be obtained from a cell line depository such as the American Type Culture Collection (ATCC, Bethesda, Md.). Such cell smooth muscle cell lines include human iliac vein smooth muscle cells (HIVS-125; ATCC accession no. CRL-2482), Syrian Golden Hamster ductus deferens smooth muscle cells (DDT1; CRL-1701), human umbilical vein smooth muscle cells (HUVS-112D: CRL-2481), rat aorta smooth muscle cells (Hep-Sa; CRL-2018), and human aortic smooth muscle cells (T/G HA-VSMC; CRL-2498). The conditions for growth of the specific cell line purchased will depend on the biological source and generally instructions for the growth of the cells are made available along with the cell lines from ATCC. In other applications, the smooth muscle cells can be obtained from the patient who will be the recipient of the tissue engineering structure. Such autologous cells can be obtained from a surgical excision or a biopsy and can be isolated, cultured, expanded or enriched according to various techniques known in the art.

In one aspect, the isolated cells or cell lines can be pluripotent (obtained by isolation or enrichment or induced dedifferentiation) and able to differentiate into cells that possess contractile function. The cells may be derived from any vertebrate or non-vertebrate animal source. For example, the animal source may be human, monkey or other primate, mouse, rat, rabbit, cat, dog, goat, sheep, pig, horse, cow, fish, bird or any other animal from which such cells may be harvested. In one aspect, the smooth muscle cells used in the three-dimensional culture are mammalian cells. In certain embodiments, the cells can be human or primate cells, but rat and rabbit cells may also be usefully employed herein. Once obtained, the cells can be cultured and the appropriate growth factors may be added to the culture. The concentration of such factors maintained in the cultures can be monitored and adjusted to optimize growth. Cells cultured in this manner can be used for transplantation or implantation in vivo. As noted above, it will often be preferable to obtain the muscle cells from the patient's own tissues (autologous cells).

The invention can be carried out with primary smooth muscle cells isolated from a variety of organs that contain smooth muscle and/or circular smooth muscle. Organs that contain circular smooth muscle include the esophagus, stomach, duodenum, jejunum, ileum, colon, trachea, bronchial tubes, uterus, blood vessels, lymphatic vessels, urethra, glandular ducts, and the ciliary muscle of the eye. For example, smooth muscle cells can be isolated from the internal anal sphincter (IAS) of New Zealand White rabbits as described previously (Bitar et al., Am J Physiol 260: G537-G542, 1991; Bitar et al., Am J Physiol 242: G400-G407, 1982).

The primary cells may be readily isolated by disaggregating an appropriate organ or tissue that is to serve as the source of the cells using standard techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. The digestive enzymes include but are not limited to trypsin, chymotrypsin, collagenase, elastase, and/or hyaluronidase, DNase and pronase. Mechanical disruption can also be accomplished by a number of methods including, but not limited to the use of grinders, blenders, sieves, homogenizers, pressure cells, or sonicators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107-126.

Once the tissue has been reduced to a suspension of individual cells, the suspension can be fractionated into subpopulations from which the myocyte and/or fibroblast cells can be obtained. Fractionation also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter current distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

Neuronal Cells

Stem cells suitable for use in the methods are multipotent cells that are capable of differentiating into neuronal cells (i.e., neurons), astrocytes and oligodendrocytes (Eriksson, P. S. et al., Nature Med. 4:1313-1317 (1998); Palmer, T. D. et al., Mol. Cell Neurosci., 8:389-404 1997).

Non-limiting examples of other cells that may be suitable for use in the methods disclosed include precursor cells that are committed to neural restricted lineages, which can generate glial cell precursors that progress to oligodendrocytes and astrocytes; and neuronal precursors that progress to neurons. Other committed precursor cells include but are not limited to glial, neuronal, astrocyte and oligodendrocyte cells.

Neuronal cells, including mature neural cells and/or undifferentiated stem and progenitor neuronal cells, may be obtained and isolated from multiple tissue types. Some non-limiting examples include the enteric nervous system, which contains numerous different neuronal populations, such as primary afferent neurons, interneurons and effector neurons; and tissues and organs of the central nervous system, such as the brain and spinal cord. Again, in certain embodiments, the neuronal precursor cells are autologous cells obtained from the patient who will be the recipient of the innervated construct.

Neuronal cells can be obtained by dissociation of individual cells from the connecting extracellular matrix of the tissue. For example, tissue from a particular neural region may be removed from the donor using a sterile procedure, and the cells dissociated using any method known in the art including treatment with enzymes such as trypsin, collagenase and the like, or by using physical methods of dissociation such as with a blunt instrument. In an aspect, dissociation of cells can be carried out in tissue culture medium. Dissociated cells may be centrifuged at low speed, between 200 and 2000 rpm, usually between 400 and 800 rpm, and then re-suspended in culture medium. The neuronal cells can then be cultured in suspension or on a fixed substrate. Cell suspensions may then be seeded in any receptacle capable of sustaining cells, particularly culture flask, culture plates or roller bottles, and more particularly in small culture flasks. Cells cultured in suspension may then be re-suspended at a desired concentration.

In one embodiment, the dissociated neuronal cells can be cultured to form neurospheres by placing the dissociated cells into any known culture medium that is capable of promoting formation of neurospheres. Such culture medium can include, for example, HEM, DMEM, RPMI, F-12, and combinations thereof. The culture medium can include supplements which are required for cellular metabolism, such as glutamine and other amino acids, vitamins, minerals and useful proteins, such as transferrin and the like. The culture medium may also contain antibiotics to prevent contamination with yeast, bacteria and fungi such as penicillin, streptomycin, gentamicin and the like. In some cases, the medium may contain serum derived from bovine, equine, chicken and the like. However, a medium for promotion of the formation of neurospheres is typically serum-free culture, as serum tends to induce differentiation and contains unknown components (i.e., is undefined). A defined culture medium can also be used if the cells are to be used for transplantation purposes. For example, the culture medium can comprise a mixture of DMEM, F12, and a defined hormone and salt mixture.

The culture medium can be supplemented with at least one neurosphere inducing growth factor and/or compound. As used herein, the term "growth factor" refers to a protein, peptide or other molecule or compound having a growth, proliferative, differentiative, or trophic effect on neuronal stem cells and/or neural stem cell progeny. Examples of growth factors can include, for example, bone morphogenetic proteins (BMPs), platelet-derived growth factor (PDGF), Sonic hedgehog (Shh), insulin-like growth factor 1 (IGF-1), epidermal growth factor (EGF), amphiregulin, acidic fibroblast growth factor (aFGF or FGF-1), basic fibroblast growth factor (bFGF or FGF-2), transforming growth factor alpha (TGFα), nerve growth factor (NGF), N2 (Invitrogen), thyrotropin releasing hormone (TRH), transforming growth factor betas (TGFβs), and combinations thereof In one aspect of the growth factors included in the culture medium can include EGF and FGF.

In another embodiment, neuronal differentiation factors, such as chemical or biological factors that induce differentiation of stem cells into cells of the neuronal lineage, can be used to differentiate the undifferentiated stem and progenitor neuronal cells into neurons. Neuronal differentiation factors can include, but are not limited to, basic fibroblast growth factor, fibroblast growth factor-8, brain-derived neurotrophic factor, Sonic Hedgehog, N2 supplement™, and combinations thereof that are capable of modulating neuronal differentiation of stem cells in culture. Neuronal cells differentiated by methods have a mature phenotype and display neuronal function. Monitoring the progress of neuronal differentiation can involve, for example, screening for expression of genetic markers of neuronal differentiation. Developmental progression of the cells in culture can be monitored, for example, by measuring levels of neuroectodermal transcripts including, but not limited to, mRNA for c-Ret, sox1, otx2, otx1, pax2, pax5, and Nurr1, nestin, GFAP, MBP, NF200, Dopamine, TH, GABA, TrH, and DBH. Assays for monitoring gene expression are well known in the art (e.g., RT-PCR), and can be conducted using standard methodology.

Separation of neuronal cells by selecting cells that express cellular characteristics or phenotypic properties, such as through immunocytochemistry (e.g., dual-label immunofluorescence and immunoperoxidase methods) with antibodies that detect cell proteins on neuronal cells, astrocytes and/or oligodendrocytes. In particular, cellular markers for neuronal cells include NSE, NF, MAP-2; and for glia, GFAP (an identifier of astrocytes), galactocerebroside (GalC) (a myelin glycolipid identifier of oligodendrocytes), and the like.

Immunocytochemistry can also be used to detect the expression of neurotransmitters, or in some cases the expression of enzymes responsible for neurotransmitter synthesis. For the identification of neuronal cells, antibodies can be used that detect the presence of acetylcholine (ACh), dopamine, epinephrine, norepinephrine, histamine, serotonin or 5-hydroxytryptamine (5-HT), neuropeptides such as substance P, adrenocorticotrophic hormone, vasopressin or antidiuretic hormone, oxytocin, somatostatin, angiotensin II, neurotensin, and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins like β-endorphin and enkephalins such as met- and leu-enkephalin, prostaglandins, amino acids such as GABA, glycine, glutamate, cysteine, taurine and aspartate and dipeptides such as carnosine. Antibodies to neurotransmitter-synthesizing enzymes can also be used, such as glutamic acid decarboxylase (GAD) which is involved in the synthesis of GABA, choline acetyltransferase (ChAT) for ACh synthesis, dopa decarboxylase (DDC) for dopamine, dopamine-β-hydroxylase (DBH) for norepinephrine, and amino acid decarboxylase for 5-HT. Antibodies to enzymes that are involved in the deactivation of neurotransmitters may also be useful such as acetyl cholinesterase (AChE) which deactivates ACh. Antibodies to enzymes involved in the reuptake of neurotransmitters into neuronal terminals such as monoamine oxidase and catechol-o-methyl transferase for dopamine, for 5-HT, and GABA transferase for GABA may also identify neurons. Other markers for neurons include antibodies to neurotransmitter receptors such as the AChE nicotinic and muscarinic receptors, adrenergic receptors $\alpha_1$, $\alpha_2$, $\beta_1$ and $\beta_2$, the dopamine receptor and the like.

Muscle and Neuronal Tissue Constructs

In one aspect of the invention, The replacement structures are bioengineered from multiple muscle and neuronal cell constructs. To generate the muscle and neuronal constructs in culture, the smooth muscle cells and neuronal cells are grown in an appropriate nutrient medium. Many commercially available media such as DMEM, RPMI 1640, Fisher's Iscove's, McCoy's, and the like may be suitable for use. In addition, the constructs should be "fed" periodically to remove the spent media and depopulate released cells.

These procedures are greatly facilitated when carried out using a bioreactor, which is a closed system housing the three-dimensional framework inoculated with muscle cells. A bioreactor reduces the possibility of contamination, maintains the cultures under intermittent and periodic pressurization to create environmental conditions that maintain an adequate supply of nutrients to smooth muscle cells throughout the cartilage tissue construct by convection.

To generate each muscle and neuronal cell construct, a homogenous smooth muscle cell population and neuronal cell population can be grown separately or together in a cell culture vessel containing one or more extracellular matrix proteins. Examples of extracellular matrix proteins can include, gelatin, gum arabic, collagens (such as collagen I, collagen II, collagen III, collagen IV, collagen V, collagen VI, collagen VII, collagen VIII, collagen IX, and collagen X), fibronectin, laminin, glycosaminoglycans, mixtures thereof, and other materials having properties similar to biological matrix molecules known to those skilled in the art of cell culture.

In particular, fibrin gels can be used in forming the constructs of the present invention. Fibrin can be obtained by the enzymatic cleavage of fibrinogen by the serine proteinase thrombin allowing the fibrin monomers to interact and form fibrils. Within a fibrin matrix, cells rapidly migrate, proliferate, and digest the fibrin replacing it with their own extracellular matrix (ECM). Grassl et al., Journal of Biomedical Material Research 60: 607-612, 2002. Grassl et al., Journal of Biomedical Materials Research 66A: 550-561, 2003. Neidert et al., Biomaterials 17: 3717-3731, 2002. Ross & Tranquillo Matrix Biology 22: 477-490, 2003).

In one embodiment, the neuronal cells also can be grown in a fibrin gel, or in a collagen or a collagen/laminin matrix. After mixture with the matrix material, the neuronal cell population can be cultured to form a layer of neuronal cells. The neuronal cell population may be cultured to coat a cylindrical ring. In one embodiment, the cylindrical ring can be made of silicone, such as those sold under the trade name Sylgard™. Additionally, the neuronal cell population may be cultured on a silicone treated surface.

The smooth muscle cells can also be grown in fibrin gel to produce a transient three-dimensional matrix. Additionally, the smooth muscle cells can be grown in a collagen or a collagen/laminin matrix to produce a transient three-dimensional matrix. The smooth muscle cell/matrix mixture can be layered over the neuronal cell population. Alternatively, the smooth muscle cell/matrix mixture can be cultured as the first layer with the neuronal cell/matrix mixture layered on top of the smooth muscle cell/matrix mixture. In another embodiment, the smooth muscle cell population and the neuronal cell population are mixed together with the matrix material and cultured simultaneously to produce a transient three-dimensional matrix.

Matrix proteins, such as fibrin, collagen and/or laminin, guide smooth muscle cells into a unidirectional formation in culture to form a functional smooth muscle cell construct. The type of matrix that may coat the cell culture vessel and cell culture vessel of the invention is virtually limitless and may include both biological and synthetic matrices. The matrix will have all the features commonly associated with being "biocompatible," in that it is in a form that does not produce an adverse, allergic or other untoward reaction when administered to a mammalian host. Such matrices may be formed from either natural or synthetic materials.

In another aspect of the invention, cylindrical molds can be used to guide or shape the constructs. Such molds can be made of silicone, such as those sold under the trade name Sylgard™. In another aspect, non-cylindrical molds can be used to guide or shape the constructs. The constructs can be formed into virtually limitless shapes and sizes.

Tissue Structures

Individual smooth muscle cell/neuronal cell constructs can be assembled to form a tissue structure. The smooth muscle cell/neuronal cell constructs can be placed on a scaffold having dimensions appropriate for the tissue contemplated. The number of smooth muscle cell/neuronal cell constructs used in the tissue structure varies depending on the size and dimensions of the tissue structure to be bioengineered. In addition, smooth muscle cell/neuronal cell constructs can be alternated with smooth muscle cell constructs or neuronal cell constructs. In an exemplary embodiment, the smooth muscle cell/neuronal cell constructs are joined to adjacent smooth muscle cell constructs or tissues that lack neuronal cells or sufficient innervation.

In one embodiment, the constructs can be joined to form the tissue structure by layering or bonding multiple contractile smooth muscle cell constructs together using standard techniques such as suturing, heating, stapling, and gluing with biological/surgical glue, or a combination of these methods. The constructs can also be joined or bonded to a scaffold, such as a tubular scaffold. Joining, gluing, layering or bonding one or more constructs together can also strengthen the tissue structure.

Glues and tissue sealants are well-known in the art and have been commercially available outside the United States for more than a decade. Glues based on gelatins cross linked with formaldehyde have been used experimentally, principally in Europe, since about 1964. Several formulations have been proposed of which "GRF" (gelatin, resorcinol, formol) is best known. Hot solutions of select gelatin are mixed in situ with a curing agent consisting primarily of formaldehyde solution. The mixture rapidly sets to a solid which adheres to tissues.

Fibrin glues utilize the natural processes of blood clot formation to generate an adhesive or sealant composition. One commercial product is "Tussicol"®, Rugis, France. Another is "Fibrin Sealant Kit 1.0" available from Osterreiehisehes Institut fur Ilaemoderivate, GMBH, subsidiary of Immuno AG, A-1220, Vienna, Austria. Two components are combined to form an artificial blood clot. One of the components is a solution of fibrinogen and blood clotting factors such as Factor XIII, and the other is primarily a solution of thrombin and calcium ion.

In another embodiment, the constructs can act as a neural patch by joining the construct with tissues or organ structures lacking sufficient innervation. The neural patch can be connected to the tissue by using standard techniques such as suturing, heating, stapling, and gluing with biological/surgical glue, or a combination of these methods. The constructs can also be joined or bonded to a scaffold prior to joining with tissues. One or more neural patches can also be joined together by gluing, layering or bonding to strengthen the tissue structure or provide additional neural sources.

Tissue Culture Vessels

Those of ordinary skill in the art will readily appreciate that the cell culture and bioengineering methodologies described herein may be carried out in a variety of environments (i.e., vessels or containers). Smooth muscle cells are anchorage dependent, and therefore to grow in culture these cells require a nontoxic, biologically inert, and optically transparent surface that will allow cells to attach and allow movement for growth. Tissue culture vessels or plates include specially-treated polystyrene plastic that are supplied sterile and are disposable. These include Petri dishes, multi-well plates, microtiter plates, roller bottles, screwcap flasks (T-25, T-75, T-150 cm.sup.2 of surface area), culture bags or any container capable of holding cells, preferably in a sterile environment.

In one embodiment of the present invention, a bioreactor is also useful for bioengineering tissue structures and culturing smooth muscle or neuronal cells. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J.

Further, patents covering such bioreactors include U.S. Pat. Nos. 6,096,532; 6,001,642, 5,985,653; 5,888,807; 5,688,687, 5,605,835, 5,190,878, which are incorporated herein by reference.

There are a number of different kinds of bioreactors, devices designed to provide a low-shear, high nutrient perfusion environment, available on the market. For example, the invention may be carried out in a rotating wall bioreactor, which consists of a small inner cylinder, and the tubular structure, positioned inside a larger outer cylinder. Although the tubular structures of the present invention can be fabricated on the inner cylinder, other locations within the bioreactor also may be used for placement of the construct as well. The gap between the inner and outer cylinders serves as the culture vessel space for cells. Culture medium can be oxygenated via an external hydrophobic membrane. The low shear environment of the rotating bioreactor promotes cell-cell and cell-extracellular matrix (ECM) interactions without the damage or "washing away" of nutrients that occurs with active stirring.

Three-Dimensional Culture System

The three-dimensional culture system of the invention can be used in a variety of applications. In one embodiment, include, the three-dimensional culture system can be used to condition either the individual smooth muscle cell/neuronal cell constructs or the bioengineered tissue structures in vitro prior to transplantation or implantation in a subject.

To generate the three-dimensional tissue structures in culture, the cells in the smooth muscle cell/neuronal cell constructs or the bioengineered tissue structures must be grown in an appropriate nutrient medium, such as commercially available medias like DMEM, RPMI 1640, Fisher's Iscove's, McCoy's, and the like. In addition, the three-dimensional cultures should be "fed" periodically to remove the spent media and depopulate released cells.

Those of ordinary skill in the art will readily appreciate that the cell culture and bioengineering methodologies described herein may be carried out in a variety of environments (i.e., vessels or containers). Smooth muscle cells are anchorage dependent, and therefore to grow in culture these cells require a nontoxic, biologically inert, and optically transparent surface that will allow cells to attach and allow movement for growth. Tissue culture vessels or plates include specially-treated polystyrene plastic that are supplied sterile and are disposable. These include Petri dishes, multi-well plates, microtiter plates, roller bottles, screwcap flasks (T-25, T-75, T-150 cm.sup.2 of surface area), culture bags or any container capable of holding cells, preferably in a sterile environment. These procedures are greatly facilitated when carried out using a bioreactor, which can be a closed system housing the three-dimensional framework inoculated with muscle cells. A bioreactor reduces the possibility of contamination, maintains the cultures under intermittent and periodic pressurization to create environmental conditions that maintain an adequate supply of nutrients to smooth muscle cells throughout the cartilage tissue construct by convection.

In one embodiment of the present invention, a bioreactor is also useful for bioengineering the constructs of the tissue structures by culturing smooth muscle cells and/or neuronal cells. For example, several manufacturers currently make devices that can be used to grow cells and be used in combination with the methods of the present invention.

These methods may be used for generating the smooth muscle/neuronal cell constructs or the bioengineered tissue structures and may be used to determine if the bioengineered tissue structures are functionally similar to naturally occurring mammalian tissue. In addition, smooth muscle cell function may be measured in vascular muscles as described in Gorenne et al., Amer. J. Physiol. 5:H131-H138, 1998.

Matrix/Scaffold Materials

It is contemplated that each bioengineered smooth muscle/neuronal cell construct may serve as a component to a larger tissue structure to replace an existing organ. The scaffold used in the formation of the bioengineered tissue structure may be removed prior to transplantation or implantation in a subject or the scaffold may be inserted as part of the bioengineered tissue structure. For insertion of the bioengineered tissue structure into a mammal in need, the matrices used in the formation of the smooth muscle/neuronal cell construct and/or the scaffold used in the formation of the bioengineered tissue structure may be fabricated from biodegradable materials that will erode over time in the body to yield a completely natural tissue. These matrices and scaffolds will not induce any chronic inflammatory responses, and cannot serve as a long-term site for infection. Biodegradable polymers have been utilized to engineer tissues that will be structurally integrated with the host tissue. A number of naturally-derived matrix-like materials may be used that will eventually biodegrade in an in vivo environment. In addition, the use of synthetic, biodegradable matrices and scaffolds will often be advantageous as the degradation time of such synthetic materials can be designed to coincide with the formation of a new tissue from the cultured cells.

The choice of matrix/scaffold material will differ according to the particular circumstances and the type of cells used (smooth muscle and/or neuronal cells) or the type of tissue to be bioengineered. Physical and chemical characteristics, such as, e.g., biocompatibility, biodegradability, strength, rigidity, interface properties and even cosmetic appearance, may be considered in choosing a matrix, as is well known to those of skill in the art. Appropriate matrices will act as an in situ scaffolding through which mammalian repair cells may migrate. Matrix/scaffold materials can also be mixtures of more than one material, either mixtures of synthetic materials, synthetic and natural materials, or natural materials.

Fibrin gel is a suitable material that may be used for organ replacement. Fibrin gel is a network made up of monomeric fibrin molecules generated by activation of fibrinogen by thrombin. This biopolymer is known to be involved in hemostasis and wound healing. Fibrin is a biodegradable material that has been used for temporary tissue replacement and as an absorbable implant material.

Another particular example of a suitable material is fibrous collagen, which may be lyophilized following extraction and partial purification from tissue and then sterilized. Matrices may also be prepared from tendon or dermal collagen as may be obtained from a variety of commercial sources, such as, e.g., Sigma and Collagen Corporation.

The various collagenous materials may also be in the form of mineralized collagen. For example, the fibrous collagen implant material termed UltraFiber™, as may be obtained from Norian Corp., (1025 Terra Bella Ave., Mountain View, Calif., 94043) may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils.

Another type of biomaterial that may be used is small intestinal submucosa (SIS). The SIS graft material may be prepared from a segment of jejunum of adult pigs. Isolation of tissue samples may be carried out using routine tissue culture techniques such as those described in Badybak et al., (J. Surg. Res. 47:74-80, 1989). SIS material is prepared by removal of mesenteric tissue, inversion of the segment, followed by removal of the mucosa and superficial submucosa by a mechanical abrasion technique. After returning the segment to its original orientation, the serosa and muscle layers are rinsed and stored for further use. Laminins are major proteins in the basal lamina, a protein network foundation for most cells and organs. The laminins are an important and biologically active part of the basal lamina, influencing cell differentiation, migration, adhesion as well as phenotype and survival.

Matrices and scaffolds may also be derived from chitin. Chitin, as used herein, refers to a polysaccharide composition prepared from the shells of arthropods, particularly crustacean or insects. It is biocompatible and naturally resorbed by the body, and has been previously used for sustained drug release, bone induction and hemostasis (see e.g. Chandy and Sharma, Biomat. Art. Cells & Immob Biotech. (1991) 19:745-760, Hou et al., Chem. Pharm. Bull. (1985) 33 (9):3986-3992, and Klokkevold, P. J. Oral Maxillofac. Sur. (1992) 50:41-45, the disclosures of which are incorporated herein by reference). Scaffolds may be manufactured with unmodified and/or modified forms chitin.

"Chitosan" is a modified form of chitin and provides one example of a suitable polysaccharide scaffold. "Chitosan," as used herein, includes any polysaccharide produced by hydrolysis of acetamido groups of N-acetyl glucosan in chitin. Also included are scaffolds derived from NOC-chitosan, a water soluble chitin derivative formed by carboxymethylation of biomedical grade chitosan. U.S. Pat. No. 4,619,995, incorporated herein by reference, sets forth the composition and preparation of NOC-chitosan. Chitin and its derivatives can be prepared in powder or solid form from freeze- or air-dried chitin, or from ground chitin as originally produced. Also included are scaffolds derived from cross-linked chitin derivatives (see e.g. Adekogbe, I. "Fabrication and characterization of DTBP-crosslinked chitosan scaffolds for skin tissue engineering" Biomaterials (2005) 26 (35):7241-50, incorporated herein by reference). Other non-limiting examples of chitin scaffolds, and methods for their manufacture, are set forth in U.S. Pat. No. 6,124,273 (disclosing chitin and chitosan hydrogels), U.S. Pat. Nos. 6,699,287 and 6,642,213, the disclosures of which are incorporated by reference.

In various embodiments, the scaffolds can be constructed from a variety of polymer compositions, including, but not limited to, chitosan, chitin, cellulose, alginate, agar, gelatin, soy protein, hyaluronic acid collagen, elastin, and silk alone or in combination with any other polymer composition, in any concentration and in any ratio. In one embodiment, the scaffolds comprise chitosan, either separately or in combination with one or more other materials. In another embodiment, chitosan may be used in combination with other materials, such as with gelatin or alginate.

Possible non-biodegradable matrices/scaffolds include non-biodegradable polymers such as semipermeable polymers such as poly(acrylonitrile-co-vinyl chloride), polylysine, cellulose acetate and polysulfone. Although generally intended for use in immobilized cells, the use of such polymers in the context of the present invention is certainly not excluded. These polymers may also be used with a variety of gels, including alginate and polyphosphazenes. Polyphosphazenes are synthetic polymers, and aqueous solutions of polyphosphazenes will gel in the presence of specific ions. These polymers can be used in the same manner as alginate. The exceedingly stable backbone of these synthetic polymers allows significant alterations in side-group functionality without losing the gentle, physiologic gelling conditions.

There are advantages and disadvantages of both natural materials, e.g., collagens, and synthetic materials, e.g., polyglycolic acids. Synthetic materials that incorporate design concepts or specific biological activities of natural biomaterials may combine the advantages of both types of materials. The reproducible, large-scale synthesis and flexible properties of synthetic polymers can be combined with the biocompatibility and biological activity of natural materials.

The matrix and scaffold materials can be made of the same material or different materials. In one embodiment, the matrix material can be collagen or collagen/laminin mixture. In another embodiment, the scaffold material can be chitosan.

In another embodiment, alginate can be used as a scaffold material, either separately or in combination with one or more other materials. Alginate is easily processed, water soluble, and non-immunogenic. Alginate is a biodegradable anionic polysaccharide with free hydroxyl groups that offer easy gelling. Alginate is a derivative of brown seaweed that has been used for a various medical applications from impression casting in dentistry to medical bandages. The ability to be cast easily and proof of biocompatibility make alginate a desirable material for use in the present invention. Alginate absorbs and holds water well, making it ideal for injury repair where a moist environment is ideal for healing.

Assays for Measuring Smooth Muscle Cell Function

The standard protocols for defining and testing gastrointestinal smooth muscle strips (contraction, relaxation, and spontaneous tone) in vivo are taught in Glavind et al., Am. J. of Physiol. 265: G792-G798, 1993, Glavind et al., Glavind et al., American Journal of Physiology 272: G1075-G1082, 1997, Chakder & Rattan, Am J. Physiol 264: G702-G707, 1993, Knudsen et al., Amer. J. of Physiol. 269: G232-G239, 1995. Following stretch of the muscle strip and a period of equilibrium, spontaneous tension/tone has been described as either steady tension oscillations or stable tension/tone for an extended period of time if undisturbed, accompanied by the ability to contract and relax with the appropriate stimulation. The bioengineered structures of the invention displayed spontaneous tension. Following stretch and stabilization of the baseline tension, bioengineered rings exhibited steady and stable tension/tone over a period of time, and change in the baseline tension was only due to agonist-induced stimuli. The stable tension generated by the rings arbitrarily set to zero for the purposes of consistent force measurements.

These methods may be used for innervated tubular tissue structures generated using any circular smooth muscle cells and may be used to determine if the bioengineered structures are functionally similar to any naturally occurring mammalian structure or isolated smooth muscle cell. The experimental design of the bioengineered structures is as follows: 1) The bioengineered tubular tissue structure generates a spontaneous basal tone. 2) Upon addition of the relaxant transmitter 8-br-AMP, 8-br-cAMP, the bioengineered structure induces a rapid and significant decrease in the basal tension/basal tone (relaxation) that is measured and expressed as decrease in force generation. 3) Upon addition of acetylcholine, acetylcholine induced a great and immediate generation of force measured (contraction). 4) Addition of 8-br-cAMP-induced rapid relaxation of acetylcholine-induced contraction and force generation of bioengineered structures.

Peristaltic forces or propulsive nature of the innervated tubular tissue structures can also be measured by methods known in the art. For example, inserting fluid into the scaffold at one end, while the other end is clamped, will expand the innervated tubular tissue structures at the midsection and allow for unidirectional flow. Upon peristaltic motion of the bioengineered tubular tissue structure, the liquid will be emptied at the opposite end it was inserted, thereby decompressing the midsection. The maximum volume of fluid the innervated tubular tissue structures can expel without signs of leakage or backflow can also be measured. Additionally, the fluid pressure can be applied several times to measure for the presence of leakage and backflow.

In addition, smooth muscle cell function may be measured in vascular muscles as described in Gorenne et al., Amer. J. Physiol. 5:H131-H138, 1998. For measurement of isometric force, arteries may be cleaned of excess connective tissue, and the endothelium is removed by gently scraping the intima with a cotton swab. Medial strips of swine carotid artery (0.5 3 7 mm) are mounted on a Muscle Research Station at room temperature and allowed to equilibrate in PSS for 90 minutes. A passive force of 100 mg is applied to all tissues. After equilibration, tissues are maximally contracted with agonists (50 µM) and then washed in PSS until basal force is recovered. The tissues are then incubated for 2 hours in either PSS or PSS containing an antagonist. After this incubation period, cumulative concentration-response curves to agonists are performed.

In some embodiments, the smooth muscle cell function is a patterned motion including at least two evoked contractions at different innervated tubular muscle structures. Optionally, the different innervated tubular tissue structures include adjacent tubular muscle structures and/or remote innervated tubular tissue structures. In some embodiments, the at least two evoked contractions are sequentially and/or timely generated according to a preset sequence. In some embodiments, the smooth muscle cell motion includes a distally advancing contraction wave, optionally though not necessarily including peristalsis. In some embodiments, use of such a system and/or method of smooth muscle cell stimulation diminishes retrograde flow. In some cases, such a method accomplishes this result by stimulating the innervated tubular muscle structures to produce a distally travelling wave of contractions that simulate natural peristalsis.

Assays for Measuring Neuronal Cell Function

Neuronal cell function can be assessed by methods known in the art. For example, the effect of drugs in the presence of nerve blockers can be studied. Comparisons of physiology of spontaneous basal tone, along with the ability to relax basal tone in response to a stimulator, such as a neurotransmitter or electrical current. Basal tone can be measured spontaneously, pre- and post-implantation of the tissue structures with little or no external stimulation. The pattern of basal tone can be measured between spontaneously, pre- and post-implantation tissue structures.

Basal tone can also be effected by drugs or external agents, such as neurotransmitters or other stimulation. Neurotransmitters useful in this method can include, but are not limited to, nNOS-blockers such as N-Nitro-L-arginine methyl ester hydrochloride, acetylcholine, dopamine, norepinephrine, epinephrine, histamine, serotonin, adenosine, anandamide, nitric oxide, γ-aminobutric acid, glutamate, and vasoactive intestinal peptide (VIP) receptor agonists Inhibitors that block basal tone, such as nifedipine, can be used to compare basal tone in spontaneously, pre- and post-implantation tissue structures.

Receptor integrity and intracellular signaling can also be observed in response to cholinergic stimulation measured in spontaneously, pre- and post-implantation tissue structures. A drop in basal tone or relaxation would suggest that intracellular signaling mechanisms in the smooth muscle are maintained, such as functional calcium channels and VIP receptors.

EXAMPLES

Example 1

Bioengineered innervated and non-innervated internal anal sphincter (IAS) constructs were made using autologous rabbit IAS smooth muscle and enteric neuronal progenitor cells. After 4 days in culture, the constructs were placed around a biodegradable composite chitosan tubular scaffold. A non-innervated muscle construct (lacking neuronal cells) was placed abutting an innervated construct (smooth muscle cells with neuronal cells) on one side. Another non-innervated muscle construct was placed 1 mm away from the innervated construct on the other side. Physiological functionality of the constructs was assessed in vitro.

Positive NADPH Diaphorase staining of the bioengineered innervated construct demonstrated the presence of nitrergic neurons.

Microscopic images showed cellular processes bridging the gap between the innervated and the non-innervated construct as early as day 4 after placing the constructs on the scaffold. At day 10, a network of differentiated neurons was microscopically observed.

The constructs were removed from the scaffold and evaluated for their physiological activities on day 20. (a) Initially intrinsically innervated construct: (i) Acetylcholine (1 μM) induced a force generation of 153 μN, which was inhibited by pre-treatment with TTX (58%) and atropine (90%) indicating the integrity of the myogenic and neuronal components of cholinergic contraction. (ii) EFS induced a relaxation of 60 μN, which was completely inhibited by pre-treatment with TTX, indicating the integrity of the neuronal component of relaxation. (b) Initially non-innervated construct placed 1 mm away from the innervated construct: (i) Acetylcholine (1 μM) induced a force generation of 80 μN, which was inhibited by pre-treatment with TTX (40%) and atropine (75%) indicating the integrity of the myogenic component and the emergence of a new neuronal component of cholinergic contraction. (ii) EFS induced a relaxation of 88 μN, which was completely inhibited by pre-treatment with TTX, indicating the emergence of newly formed functional inhibitory motor neurons.

This is the first demonstration of a neuromuscular patch used to innervate non-innervated muscle. This provides new avenues for regenerative medicine therapeutics for neuromuscular diseases of the gut.

Example 2

In this example, intrinsically innervated three-dimensional rabbit colon constructs were bioengineered and characterized.

Smooth muscle cells were trypsinized and neurospheres were accutased. 500 k smooth muscle cells and 200 k enteric neuronal progenitor cells were centrifuged to form a cell pellet.

The enteric neuronal progenitor cells were resuspended in a 0.4 mg/ml collagen (type I rat tail) and laminin (5 ug/ml) solution. The solution was pipetted onto Sylgard coated 35 mm dishes around a central post. When placed in the 37 C incubator, solution gelled in 15-30 minutes.

Smooth muscle cell pellet was resuspended in a 0.4 mg/ml collagen solution and pipetted over the first gel layer and returned to the incubator.

After 2-4 hours, gels were released from the edge of the plate using a sterile 22 g needle.

1 ml of Neuronal Differentiation Medium (Neurobasal A+B27) was added and the plates were returned to the 37 C/7% CO2 incubator for differentiation.

Reagents: All cell culture reagents including growth medium and supplements were purchased from Invitrogen (Carlsbad, Calif.). Growth media for smooth muscle consisted of Dulbecco's modified Eagle medium (DMEM) supplemented with 10% fetal bovine serum (FBS), 1.5% antibiotic-antimycotic, and 0.6% l-glutamine. Growth media for neural progenitor cells consisted of neurobasal, N2 supplement and antibiotic-antimycotic. Neural differentiation media consisted of neurobasal medium-A supplemented with fetal calf serum, B27 supplement and antibiotic-antimycotic. Collagenase type II was purchased from Worthington Biochemicals (Lakewood, N.J.). Type I rat tail collagen was purchased from BD Biosciences (Bedford, Mass.), and Hank's balanced salt solution (HBSS) was purchased from Hyclone (Logan, Utah).

Medium molecular weight chitosan (75-85% deacetylation), glycosaminoglycan heparan sulfate, 1-ethyl-3-(3-dimethylaminopropyl)carbodiimide (EDC), acetylcholine (ACh), vasoactive intestinal peptide (VIP) and tetrodotoxin (TTX) were purchased from Sigma (St. Louis, Mo.). Sylgard [poly(dimethylsiloxane); PDMS] was from World Precision Instruments (Sarasota, Fla.).

Isolation of rabbit colonic circular smooth muscle cells: Rabbit colonic circular smooth muscle cells (RCSMCs) were isolated from rabbit sigmoid colon. Briefly, colon tissue was cleaned and washed in ice-cold HBSS. The serosa, longitudinal smooth muscle and mucosa were removed. The circular smooth muscle was finely minced, digested twice in type II Collagenase (Worthington), and filtered to eliminate cellular debris. Digested cells were washed, resuspended in growth media and plated on tissue culture flasks. Cells were grown to confluence before use in the experiments.

Isolation of rabbit neural progenitor cells: Neuronal progenitor cells were isolated from rabbit jejunum. Briefly, a biopsy of rabbit jejunum was cleaned of any material using HBSS. The tissue was minced and digested in a collagenase/dispase mixture. The cell suspension was then filtered through a 40 μm mesh and plated on petri dishes.

Fabrication of composite chitosan scaffold: Composite chitosan scaffolds were prepared with a 2 w/v % chitosan solution was mixed with type I collagen (0.1 mg/ml) in a volume ratio of 1:1. The mixture was poured into a tubular mold with a central opening, frozen at −80° C. for 3 h and then lyophilized for 24 h. The scaffolds were neutralized in 0.2 m NaOH and covalently cross linked with heparan sulfate using carbodiimide. The scaffolds were then washed several times with PBS and distilled water. The scaffolds were UV sterilized and then coated with laminin (0.05 mg/ml) to enhance neural migration for 2 hours at room temperature.

Intrinsically innervated three-dimensional circular smooth muscle constructs were bioengineered. Collagen/laminin gel containing $2 \times 10^5$ rabbit neural progenitor cells was laid down on a Sylgard-coated plate with a central cylindrical post. A second layer of collagen gel containing $5\times10^5$ rabbit colon circular smooth muscle cells was laid down on top of the first layer of gel. After gelation, neural differentiation media was added to the plate and incubated at 37° C. Non-innervated rabbit colon constructs were bioengineered by laying down $5\times10^5$ rabbit colon circular smooth muscle cells in collagen gel on a Sylgard-coated plate with a central post. After gelation, the same neural differentiation media was added to the plate. Innervated smooth muscle constructs were fixed and paraffin-embedded Immunostaining analysis for α-smooth muscle actin (F3777; Sigma) and smooth muscle specific Caldesmon (c-4562; Sigma) were performed.

At day 4, the innervated smooth muscle tissue constructs were placed next to the non-innervated smooth muscle constructs around the same tubular composite chitosan scaffold. The scaffolds with the constructs were left in neural differentiation media for a period of 18-20 days. Microscopic analysis: Five days post-placing the constructs around the scaffold, microscopic analysis of the junction between the innervated and non-innervated bioengineered smooth muscle constructs was evaluated. Microscopic analysis was performed to determine whether neural progenitor cells started differentiating and forming a neuronal network along with the attached non-innervated construct.

Eighteen to twenty days post placing them around the scaffolds, constructs were taken off and microscopic analysis was conducted on each construct.

Physiologic function: The protocol for physiologic functionality was described previously. An isometric force transducer (Harvard Apparatus, Holliston, Mass.) was used to record real time force generated by the constructs. The constructs were kept incubated in a warm tissue bath keeping the tissue samples at conditions of 37° C. ±1° C. The bioengineered tissue constructs (innervated and non-innervated constructs) were taken off the scaffold at day 15 for force generation measurement. One side of the tissue constructs was looped around the measuring arm of the transducer and the other side was attached to a fixed reference pin. Tissue constructs were allowed to equilibrate in the tissue bath containing fresh medium. All reported values of force represent active tension produced as a result of the tissue. After establishment of baseline, a 10%-15% stretch was applied to the tissues using the micromanipulator. The stretch baseline established by the tissue samples was arbitrarily set to zero and the values represent change in force generation.

Testing protocols were designed to determine the possibility of neo-innervating the smooth muscle construct attached to the innervated construct around the scaffold. Relaxation was evaluated by studying the effect vasoactive intestinal peptide (VIP) and electrical field stimulation, in the absence and presence of nerve blocker tetrodotoxin (TTX). Electromechanical coupling was tested using potassium chloride (KCl) in the presence of calcium channel blocker nifedipine. Cholinergic contraction was studied using acetylcholine (Ach) in the absence and presence of TTX. The tissues were washed with fresh buffer between each experiment.

Immunofluorescence: Innervated and non-innervated constructs were taken off the scaffold at days 18-20 and fixed in 3.7% formaldehyde overnight. Constructs were paraffin-embedded and cross sections of 6 µm thickness were obtained Immunofluorescence stainings for α-smooth muscle actin (F3777; Sigma), smooth muscle specific Caldesmon (c-4562; Sigma) and neuron specific β-III tubulin (ab25770, Abcam) were performed. Fluorophore-conjugated secondary antibodies were used to detect immunofluorescence using a Nikon Ti-E fluorescence microscope.

Cell infiltration: After taking off the constructs, the scaffolds were fixed in 3.7% formaldehyde and embedded in paraffin for histological analysis. Hematoxylin and eosin (H&E) stain was used to determine smooth muscle cell infiltration from the constructs into the scaffold.

Data analysis: GraphPad Prism 5.01 for Windows (GraphPad Software, San Diego Calif.) was used to analyze acquired data. All values were expressed as means and SEM of 3-6 experiments. Second order Savitzky-Golay smoothing was applied to raw data. A p-value less than 0.05 was considered significant.

Microscopic analysis: Rabbit colon circular smooth muscle cells were laid down along with rabbit enteric neural progenitor cells in a collagen/laminin gel. Neural differentiation media was supplied to the constructs every other day. FIG. 1 shows a fully formed bioengineered innervated colon smooth muscle construct. Microscopic evaluation of the innervated construct at day 4 showed that the enteric neural progenitor cells were arranged towards the periphery of the construct. Initial differentiation and axonal projections were observed in the construct. Immunofluorescence assays demonstrated the positive stain for α-smooth muscle actin and smooth muscle specific Caldesmon, indicating smooth muscle phenotype.

Bioengineered constructs were used at day 4 post-forming A smooth muscle construct containing neural progenitor cells was placed attached to a smooth muscle construct lacking neural progenitor cells around the same composite chitosan scaffold. The scaffold along with the constructs was incubated in neural differentiation media. Day 5 post-placing the constructs around the scaffold, microscopic evaluation of the junction between the 2 constructs showed elongated cellular processes bridging the constructs and forming a continuous network.

At days 16-18, both tissue constructs were taken off the scaffold and microscopic analysis showed the construct contained neural progenitor cells with axonal projections forming in the construct. Axonal projections were also visualized in the smooth muscle construct that was initially lacking any neuronal component, indicating the emergence of new neuronal component.

Physiologic functionality: At days 18-20 post-placing them around the composite chitosan scaffold, the constructs were taken off the scaffold and their physiological functionality was assessed using real time force generation.

Figure 2:
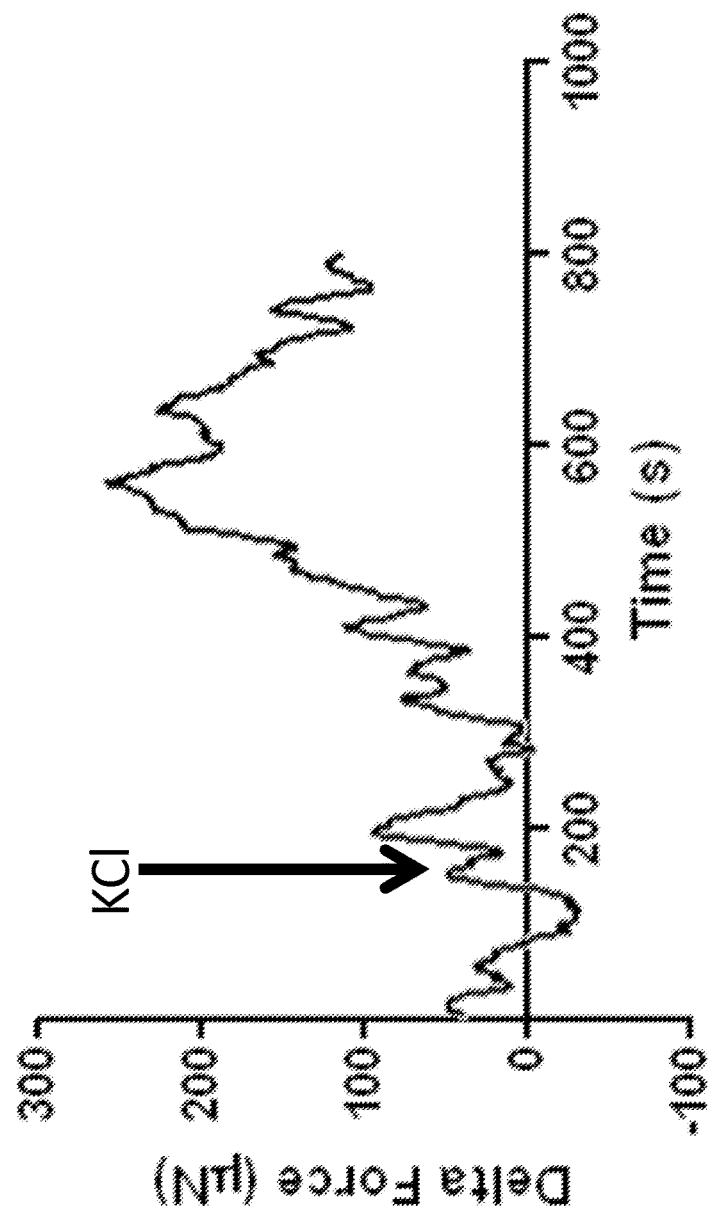
FIG. 2 is a graph showing the electromechanical coupling integrity in the innervated smooth muscle construct.
Figure 3:
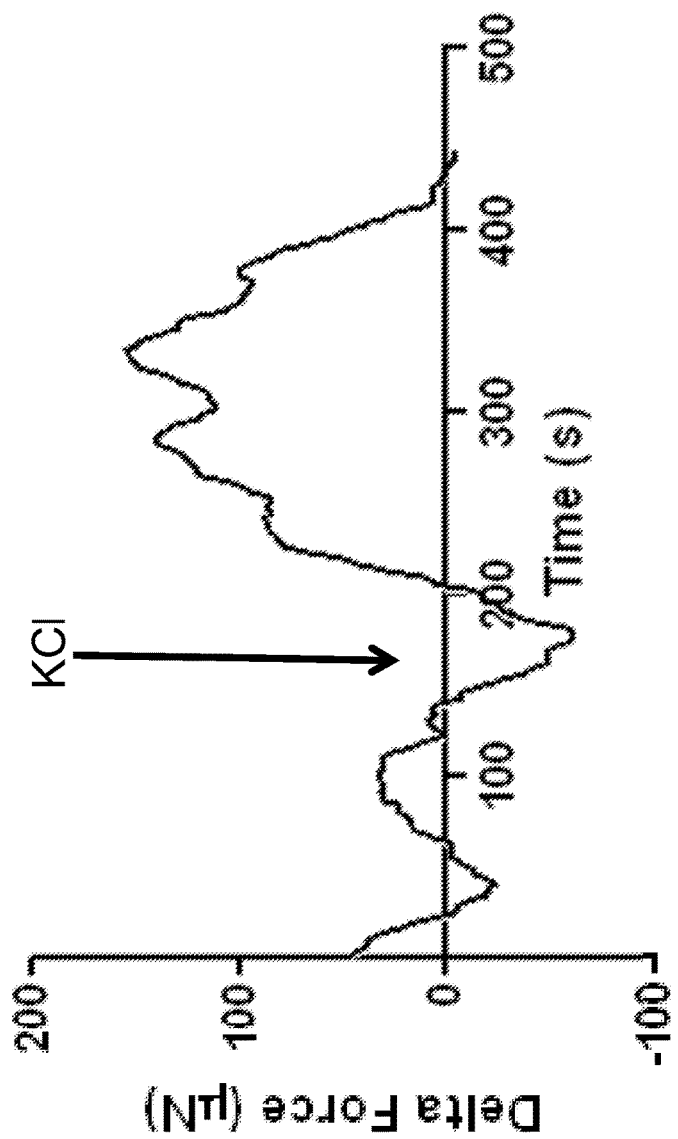
FIG. 3 is a graph showing the electromechanical coupling integrity in the non-innervated smooth muscle construct.

To test the electromechanical coupling integrity in the smooth muscle, the constructs were treated with 60 mM KCl. A rapid-rising contraction was generated in both the intrinsically innervated (FIG. 2) and non-innervated (FIG. 3) constructs. An average contraction of 300±24 µN was seen in the innervated constructs and 224±42 µN in the non-innervated constructs. In the presence of calcium channels blockers nifedipine, the same concentration of KCl did not induce a contraction in both constructs (green tracings) suggesting the presence and maintenance of calcium channels in these constructs. Response to KCl shows the maintenance of the integrity of the smooth muscle component.

Figure 4:
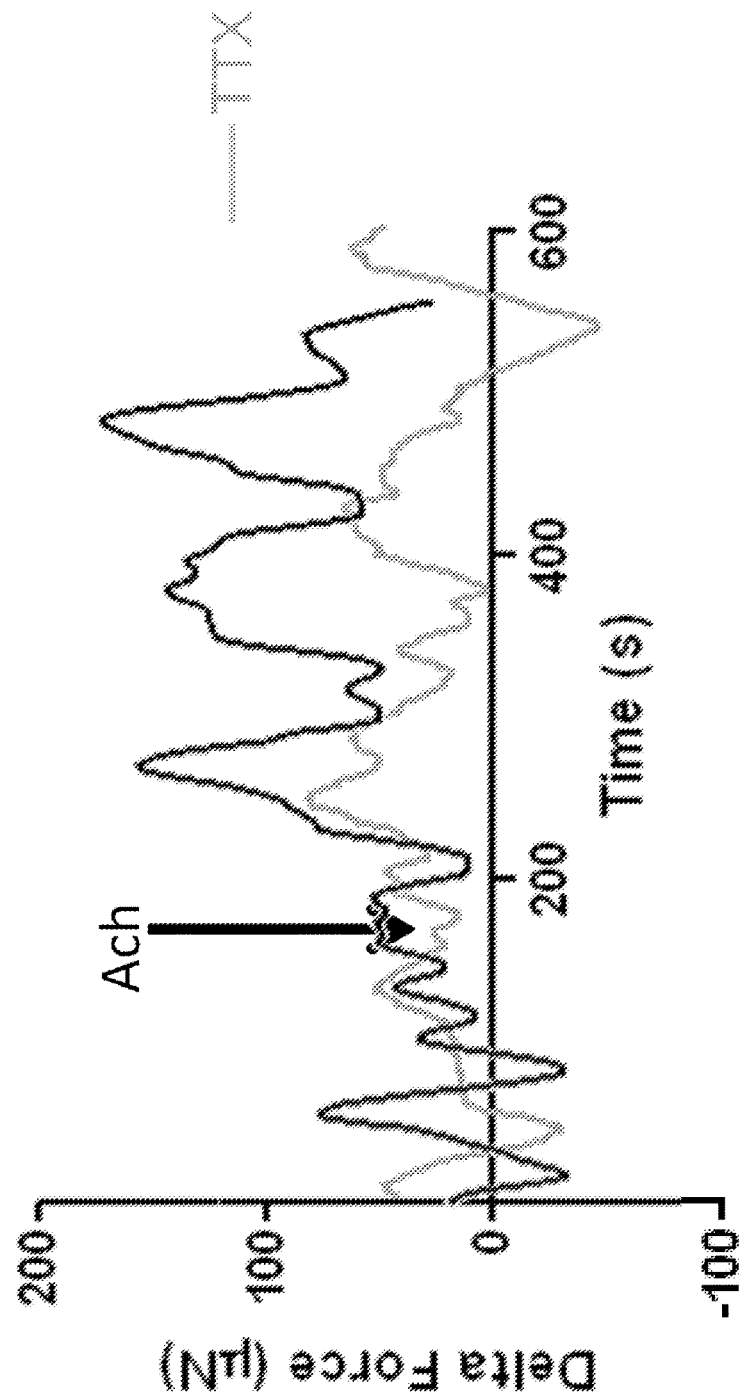
FIG. 4 is a graph showing the cholinergic contraction using acetylcholine (black line) and contraction in the presence of the neuronal blocker tetrodotoxin (TTX) (gray line) of the intrinsically innervated construct.
Figure 5:
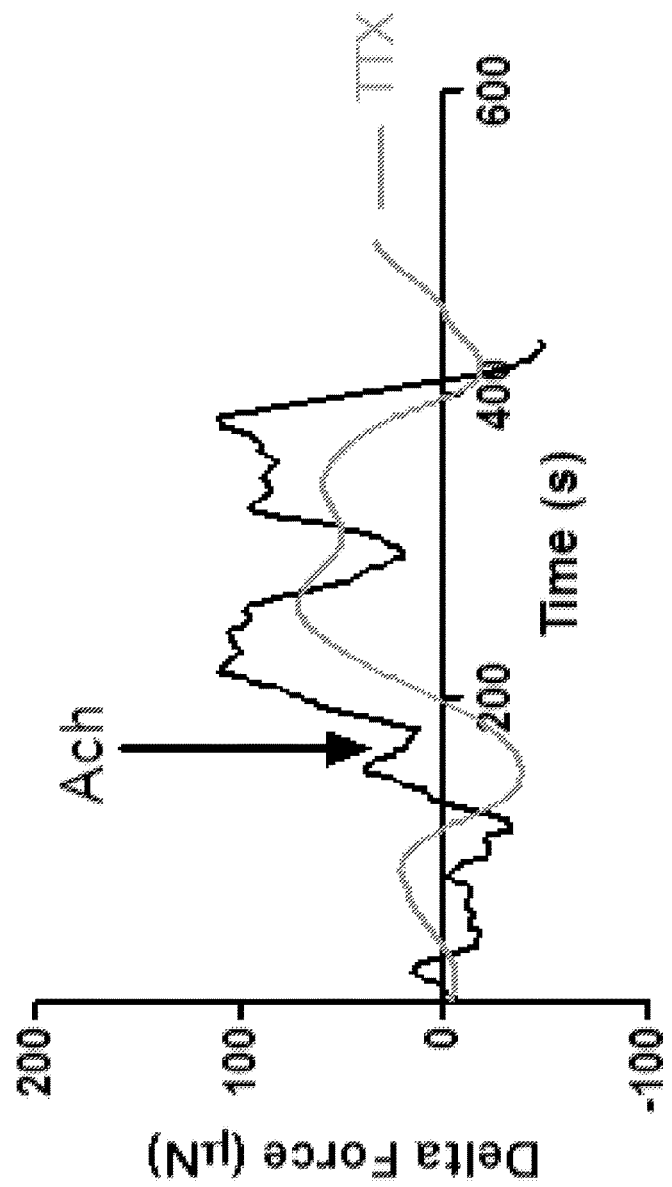
FIG. 5 is a graph showing the cholinergic contraction using acetylcholine (black line) and contraction in the presence of the neuronal blocker TTX (gray line) of the initially non-innervated construct.

Cholinergic contraction was studied using acetylcholine (Ach). Treatment of both constructs with 1 µM Ach induced immediate contractions in both intrinsically innervated constructs (FIG. 4, black line) and initially non-innervated constructs (FIG. 5, black line). Average contractions were 150±24 µN for innervated tissues and 130±28 µN for non-innervated tissues. Peak maximal contractions in the intrinsically innervated constructs were attenuated by 50-60% in the presence of the neuronal blocker TTX (FIG. 4, gray line). Similarly, TTX reduced the maximal contraction in the initially non-innervated constructs (FIG. 5, gray line). Constructs were able to return back to the resting basal force. In both constructs, contractile responses induced by the excitatory neurotransmitter Ach displayed both neuronal as well as myogenic characteristics.

Figure 6:
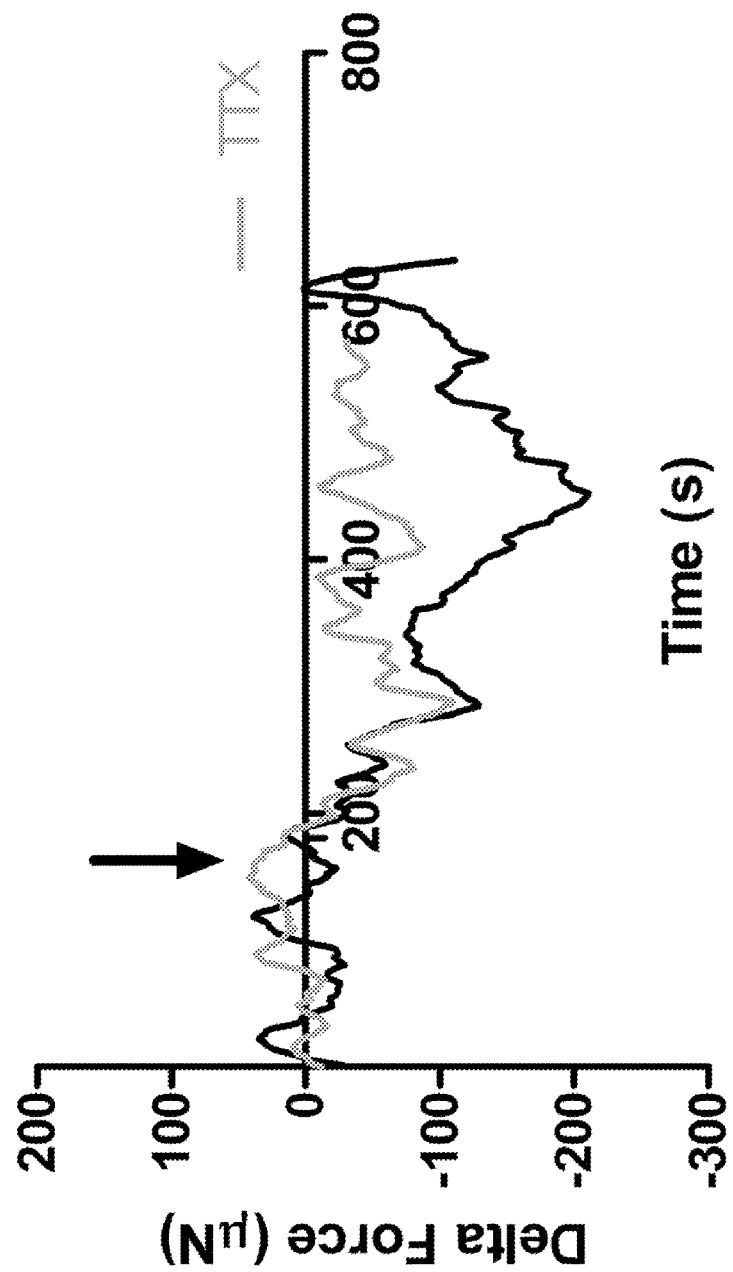
FIG. 6 is a graph showing relaxation by treatment with vasoactive intestinal peptide (VIP) and relaxation in the presence of the neuronal blocker TTX (gray line) of the innervated construct.
Figure 7:
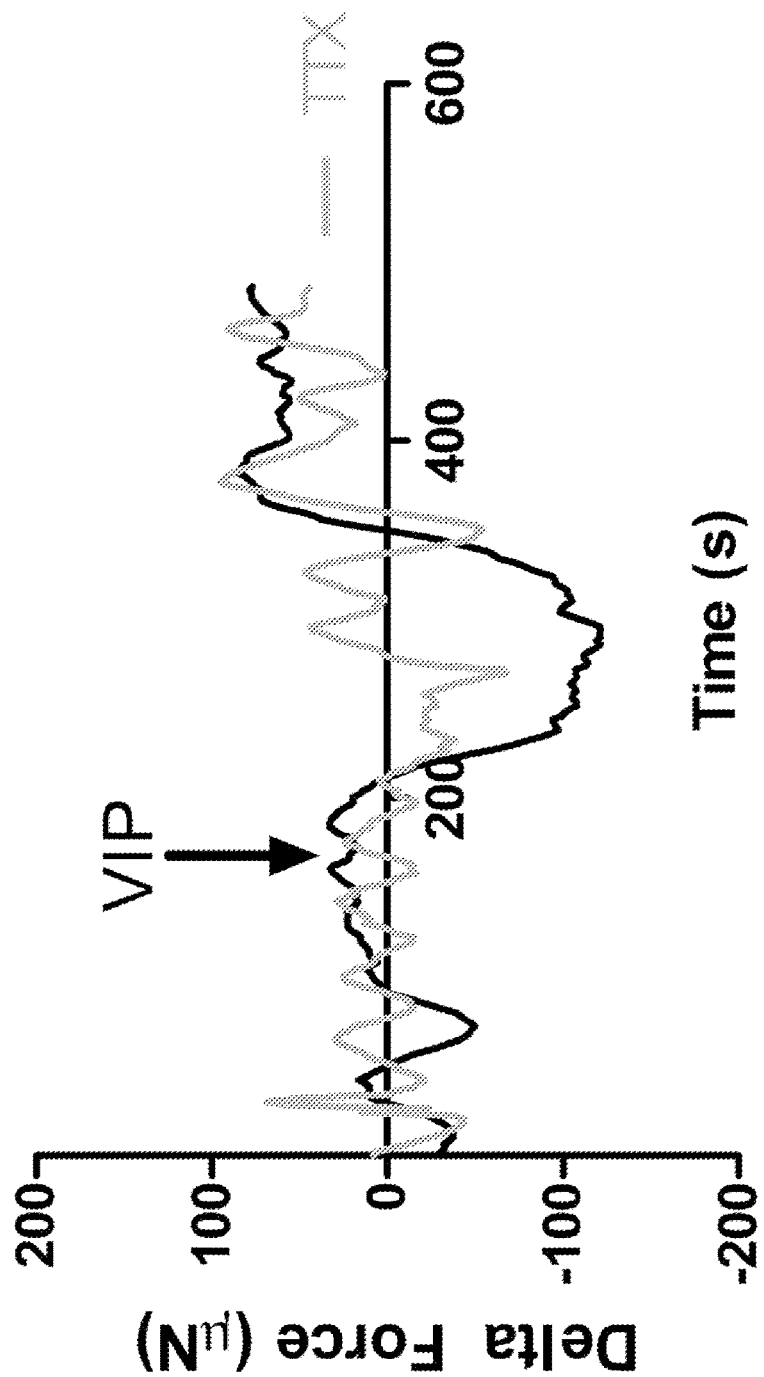
FIG. 7 is a graph showing relaxation by treatment with VIP (black line) and relaxation in the presence of the neuronal blocker TTX (gray line) of the non-innervated construct.

Relaxation of these constructs was studied by treatment with VIP. Addition of 1 µM VIP induced a rapid decrease of baseline with a maximal relaxation averaging 145±15 µN in the innervated constructs (FIG. 6, black line) and 120±18 µN in the non-innervated constructs (FIG. 7, black line). In the presence of TTX, the same concentration of VIP induced an attenuated relaxation (60% inhibition) in the intrinsically innervated constructs (FIG. 6, gray line). TTX also inhibited (50%) the relaxation in response to VIP in the initially non-innervated constructs (FIG. 7, gray line). The physiology of both constructs in response to VIP and TTX indicates the presence of myogenic and neuronal component involved in the response.

Figure 8:
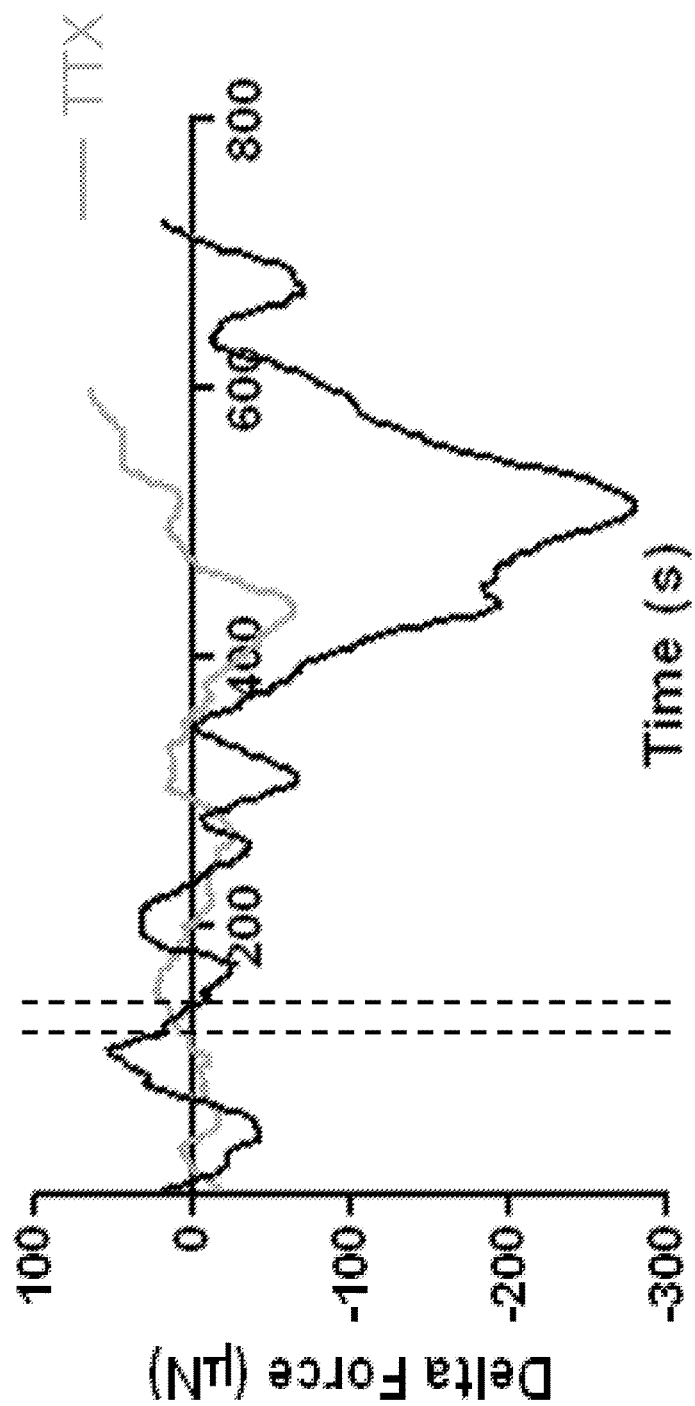
FIG. 8 is a graph showing electric stimulation to induce rapid relaxation of the basal force followed by recovery back to baseline (black line) and stimulation in the presence of the neuronal blocker TTX (gray line) of the innervated construct.
Figure 9:
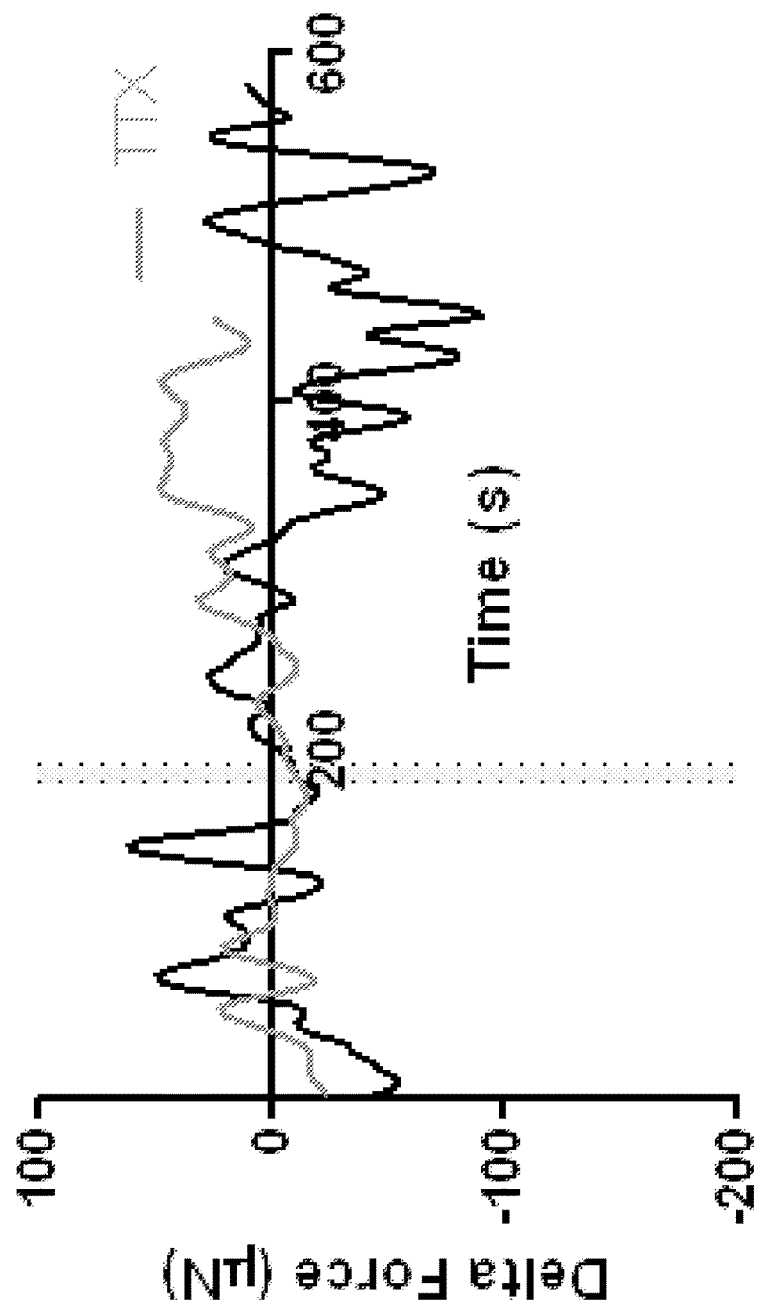
FIG. 9 is a graph showing electric stimulation to induce rapid relaxation of the basal force followed by recovery back to baseline (black line) and stimulation in the presence of the neuronal blocker TTX (gray line) of the non-innervated construct.

Electric stimulation (EFS) of the bioengineered intrinsically innervated smooth muscle constructs at 8 Hz, 0.9 ms on time induced a rapid relaxation of the basal force followed by recovery back to baseline (FIG. 8, black line). An average relaxation of 291±13 µN was assessed in the intrinsically innervated constructs. Preincubating these constructs with TTX completely abolished the response to EFS indicating that the relaxation originated from the stimulation of fully differentiated intrinsic neurons (FIG. 8, gray line). Same parameters of EFS applied to the initially non-innervated constructs caused a relaxation (FIG. 9, black line) with an average of 125±15 µN. The relaxation was completely blocked in the presence of TTX (FIG. 9, gray line). This indicates that the relaxation was neuronally mediated in these constructs.

Innervated and non-innervated bioengineered smooth muscle constructs were taken off the scaffold and fixed in 3.7% formaldehyde. Tissue samples were dehydrated and embedded in paraffin. Cross-sections of the intrinsically innervated constructs stained positive for the neuron-specific marker β-III tubulin confirming the innervation of the tissue. Neo-innervation of the initially non-innervated constructs was depicted by the positive stain with β-III tubulin. Immunofluorescence demonstrated the presence of fully differentiated neurons in both constructs.

Histological analysis provides an insight on whether smooth muscle cells have infiltrated from the constructs through the pores of the scaffold. H&E stain was performed on the scaffold alone after taking off the constructs. Stains showed no cellular content in the scaffold suggesting that the constructs retained integrity without losing cells into the scaffold.

Other embodiments and uses will be apparent to those skilled in the art from consideration of the specification and practice of the methods and constructs disclosed herein. All U.S. Patents and other references noted herein for whatever reason are specifically incorporated by reference. The specification and examples should be considered exemplary only with the true scope and spirit of the invention indicated by the following claims.

What is claimed is:

1. A method of generating an innervated muscle construct comprising
   obtaining smooth muscle cells;
   obtaining neuronal progenitor cells;
   preparing the neuronal progenitor cells by suspending the neuronal progenitor cells in a first matrix material comprising fibrin or collagen;
   preparing the smooth muscle cells by suspending the smooth muscle cells in a second matrix material comprising fibrin or collagen;
   seeding the cells by depositing the first and second cell-seeded matrix materials in contact with each other onto a culture plate;
   inducing differentiation of the neuronal progenitor cells
   culturing the seeded cells to form an innervated smooth muscle cell construct of directionally oriented smooth muscle cells; and
   removing the innervated smooth muscle cell construct from the culture plate and disposing the innervated muscle construct around a tubular scaffold.

2. The method of claim 1 wherein the step of preparing the neuronal progenitor cells further comprises suspending the neuronal progenitor cells as neurospheres in a biocompatible solution.

3. The method of claim 1 wherein the step of preparing the neuronal progenitor cells further comprises suspending the neuronal progenitor cells in a collagen/laminin solution.

4. The method of claim 1 wherein the step of preparing the smooth muscle cells further comprises suspending the smooth muscle cells in a collagen solution.

5. The method of claim 1 wherein the step of inducing differentiation of the neuronal progenitor cells further comprises exposure to Neurobasal A medium.

6. The method of claim 1 wherein the step of inducing differentiation of the neuronal progenitor cells further comprises exposure to a B-27 supplement.

7. The method of claim 1 wherein the tubular scaffold comprises chitosan.

8. The method of claim 1 wherein the method further comprises connecting two or more of the innervated muscle constructs together to form an elongated composite construct.

9. The method of claim 1 wherein the method further comprises culturing the construct in a bioreactor until it exhibits contractions in response to contractile stimulation.

10. The method of claim 1 wherein the step of preparing the neuronal progenitor cells further comprises suspending the neuronal progenitor cells in a collagen solution.

11. The method of claim 10 further comprising allowing the neuronal progenitor cell/collagen solution to gel.

12. The method of claim 1, wherein the culture plate has a central post to induce formulation of a tubular innervated smooth muscle cell construct.

13. The method of claim 12 wherein the method further comprises removing the tubular innervated muscle construct from the central post of the culture plate and disposing the construct around the tubular scaffold.

14. The method of claim 1 wherein the method further comprises connecting the innervated muscle construct to a non-innervated muscle construct to form an elongated composite construct.

15. The method of claim 14 further comprising allowing neural cells from the innervated muscle construct to infiltrate the non-innervated muscle construct.

* * * * *